United States Patent
Lee et al.

(10) Patent No.: US 10,392,468 B2
(45) Date of Patent: Aug. 27, 2019

(54) HIGHLY FUNCTIONAL NATURAL MATERIAL-DERIVED EPOXY RESIN, PREPARATION METHOD THEREFOR, AND EPOXY RESIN CURING COMPOSITION USING SAME

(71) Applicant: KUKDO CHEMICAL CO., LTD., Seoul (KR)

(72) Inventors: Hye Seung Lee, Seoul (KR); Jae Il Kim, Seoul (KR)

( * ) Notice: Subject to any disclaimer, the term of this patent is extended or adjusted under 35 U.S.C. 154(b) by 0 days.

(21) Appl. No.: 15/953,737

(22) Filed: Apr. 16, 2018

(65) Prior Publication Data

US 2018/0230261 A1    Aug. 16, 2018

Related U.S. Application Data

(62) Division of application No. 15/316,804, filed as application No. PCT/KR2015/005742 on Jun. 9, 2015, now abandoned.

(30) Foreign Application Priority Data

Jul. 18, 2014    (KR) .................. 10-2014-0091096

(51) Int. Cl.
  *C08G 59/26*    (2006.01)
  *C07D 493/04*    (2006.01)
  *C08G 59/44*    (2006.01)
  *C08G 59/50*    (2006.01)
  *C08G 59/04*    (2006.01)
  *C08G 59/42*    (2006.01)

(52) U.S. Cl.
  CPC ........... *C08G 59/26* (2013.01); *C07D 493/04* (2013.01); *C08G 59/04* (2013.01); *C08G 59/42* (2013.01); *C08G 59/44* (2013.01); *C08G 59/504* (2013.01)

(58) Field of Classification Search
  CPC ...... C08G 59/26; C08G 59/44; C08G 59/504; C08G 59/04; C08G 59/42; C07D 493/04
  USPC .......................................................... 525/526
  See application file for complete search history.

(56) References Cited

U.S. PATENT DOCUMENTS

2008/0009599 A1*  1/2008  East ................... C07D 493/04
                                                       528/1

FOREIGN PATENT DOCUMENTS

JP          2006-312702 A     11/2006
WO   WO-2012041816 A1 *  4/2012  .......... C07D 301/26

OTHER PUBLICATIONS

The Future of Epoxy Resin, Bioplastics news, Jan. 8, 2014. (page 2) http://bioplasticsnews.com/2014/01/08/fiire-of-epoxy-resin/.
J. Hong et al., Advanced materials from corn: isosorbide-based epoxy resins. Polymer Chemistry. 2014, vol. 5, pp. 5360-5368. (Abstract, Fig. 7 and method 3).

* cited by examiner

*Primary Examiner* — David T Karst
(74) *Attorney, Agent, or Firm* — Lee & Associates, LLC; Jake K. Lee

(57) ABSTRACT

Disclosed are a highly functional natural material-derived epoxy resin, a preparation method therefor, and an epoxy resin curing composition using the same. The highly functional natural material-derived epoxy resin represented by chemical formula 1 is obtained by reacting a compound, represented by chemical formula 2, and epichlorohydrin (ECH), which is obtained by using glycerin as a starting material, in the presence of a hydroxide salt.

2 Claims, 5 Drawing Sheets

HIGHLY FUNCTIONAL NATURAL MATERIAL-DERIVED EPOXY RESIN, PREPARATION METHOD THEREFOR, AND EPOXY RESIN CURING COMPOSITION USING SAME

CROSS-REFERENCE TO RELATED APPLICATIONS

This patent application is a divisional application of U.S. patent application Ser. No. 15/316,804 filed on Dec. 6, 2016, which is a national stage application of International Patent Application No. PCT/KR2015/005742 filed on Jun. 9, 2015, which claims priority to Korean Patent Application No. 10-2014-0091096 filed on Jul. 18, 2014, the entire contents of which are incorporated by reference herein.

TECHNICAL FIELD

The present invention relates to a highly functional natural material-derived epoxy resin, a method of preparing the same and an epoxy resin curing composition containing the same. More specifically, the present invention relates to a highly functional natural material-derived epoxy resin prepared by reaction of isosorbide derived from sugar (carbohydrate) with epichlorohydrin (ECH) derived from glycerin, a method of preparing the same and an epoxy resin curing composition containing the same.

BACKGROUND

Currently used bisphenol-based epoxy resins are widely used in a variety of fields including coating, adhesive agents, electrical and electronic engineering, and civil engineering and construction, due to advantages of excellent adhesive strength, mechanical properties and chemical resistance, and less shrinkage deformation during curing. Chemical materials containing the bisphenol-based epoxy resin as a main ingredient are derived from petroleum and produce chemicals harmful to human such as endocrine disruptors during the production and use.

Commonly used chemical materials containing the bisphenol-based epoxy resin as a main ingredient are derived from petroleum resources and use of irreversible fossil resources is considered to cause remarkable environmental costs. Accordingly, research is underway to obtain petroleum resource-derived bisphenol-based epoxies from recyclable resources and the most representative recyclable resources are monomers called "isosorbide (1,4:3,6-dianhydrosorbitol), isoidide (1,4:3,6-dianhydroiditol), and isomannide (1,4:3,6-dianhydromannitol)" using carbohydrate-based natural materials as sources. Research to prepare epoxies using isosorbide instead of bisphenol A has been conducted (East A, Jaffe M, Zhang Y, Catalani L H. US patent 20080021209, 2008).

This research is conducted by reaction at 115° C. for 12 hours using ECH derived from propylene, which is a petroleum resource, thus having problems of low economic efficiency and industrial inapplicability.

SUMMARY

Therefore, as a result of thorough review on the points described above, the inventors of the present invention suggested a method of preparing a 100% biomass-derived epoxy resin by reacting carbohydrate-derived isosorbide with glycerin-derived ECH under optimum reaction conditions.

Therefore, it is one object of the present invention to provide a method of preparing a natural material-derived highly functional epoxy resin that can replace conventional petroleum resource-derived bisphenol-based epoxy compounds and is thus industrially applicable owing to eco-friendliness and high yield and economic efficiency.

It is another object of the present invention to provide an epoxy curing composition containing the natural material-derived highly functional epoxy compound.

In accordance with an aspect of the present invention, the above and other objects can be accomplished by the provision of a natural material-derived compound represented by the following Formula 1:

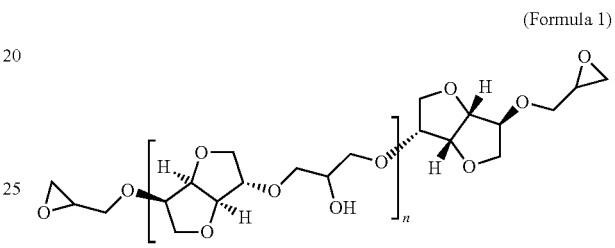

(Formula 1)

wherein n is an integer of 0 to 300.

The compound represented by Formula 1 according to the present invention is a natural material-derived isosorbide epoxy compound having a molecular structure in which two epoxy groups are linked to an isosorbide skeleton.

The natural material-derived isosorbide used for the method of the present invention has a structure represented by the following Formula 2:

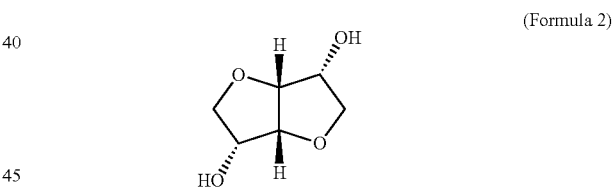

(Formula 2)

That is, according to the present invention, carbohydrate natural material-derived isosorbide (Formula 2) is used as a basic skeleton so that it is utilized in eco-friendly application fields, food and human-contact application fields, instead of bisphenol A, which is derived from a petroleum resource and issued as an endocrine disruptor.

In addition, natural material-derived epichlorohydrin (biobased epichlorohydrin) used for the present invention is obtained from glycerin, instead of propylene, as a starting material and a preparation process thereof is depicted by the following Reaction Scheme 1:

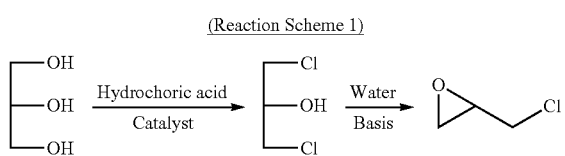

(Reaction Scheme 1)

The method of preparing Formula 1 according to the present invention may include the following steps: (Reaction Scheme 2)

1) a first step of conducting preliminary reaction of the compound represented by Formula 2 with epichlorohydrin (ECH) obtained from glycerin as a starting material in the presence of a small amount of an aqueous solution of a hydroxide salt such as sodium hydroxide;

2) conducting main reaction of the reactants of the first step at a reduced pressure;

3) a third step of standing the reaction solution after reaction of the second step, separating the supernatant by reverse aliquoting and filtering the same; and 4) a fourth step of collecting epichlorohydrin from the filtrate.

(Reaction Scheme 2)

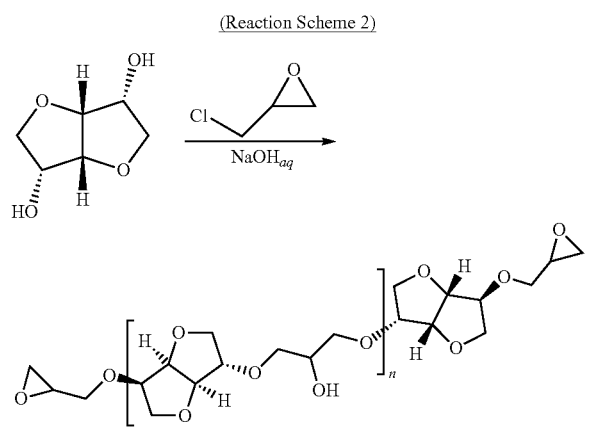

First Step

In this step, the compound represented by Formula 2 (isosorbide) is reacted with epichlorohydrin in the presence of a hydroxide salt to prepare chlorohydrin.

In the present invention, the compound represented by Formula 2 may be derived from a carbohydrate polymer. Specifically, the compound represented by Formula 2 may be prepared from the carbohydrate polymer, as depicted by the following Reaction Scheme 3.

(Reaction Scheme 3)

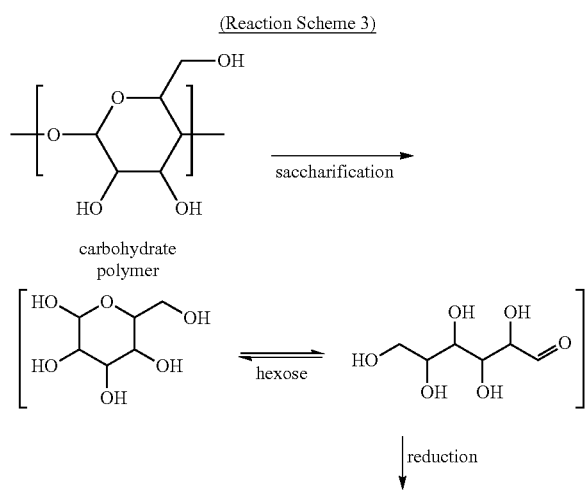

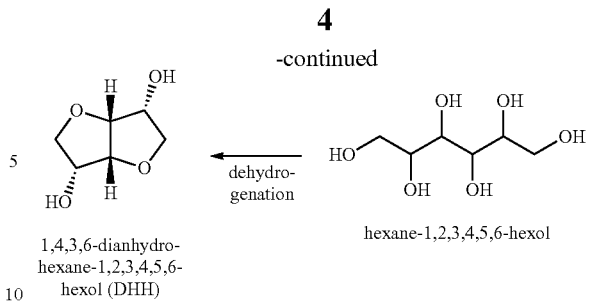

1,4,3,6-dianhydro-hexane-1,2,3,4,5,6-hexol (DHH)

hexane-1,2,3,4,5,6-hexol

First, a carbohydrate polymer such as cellulose present in an amount of about 30 to about 40% in a terrestrial plant is extracted and subjected to hydrolysis or saccharification including treatment with an enzyme to obtain a hexose compound, an aldehyde group of the hexose compound is reduced by hydrogenation or the like to prepare hexane-1, 2,3,4,5,6-hexol having six hydroxyl groups, and the compound is subjected to cyclization using dehydrogenation under the condition of an acidic catalyst to obtain a compound represented by Formula 2 as a bicyclic compound in which two five-numbered rings are fused.

In the present invention, the first step is carried out by reacting isosorbide (Formula 2) with epichlorohydrin in the presence of a hydroxide salt, which provides reaction conditions for producing chlorohydrins by reacting isosorbide (Formula 2) with epichlorohydrin.

The hydroxide salt is composed of an alkali metal and a hydroxyl group and, specifically, for example includes one or more selected from LiOH, NaOH, KOH and the like, but the present invention is not limited thereto.

Regarding a weight ratio between the compound represented by Formula 2 and epichlorohydrin, which are the reactants of the first step, it is effective that epichlorohydrin is preferably present in an amount of 200 to 1,300 parts by weight, more preferably 550 to 650 parts by weight, with respect to 100 parts by weight of the compound represented by Formula 2. When the epichlorohydrin is present in an amount lower than 200 parts by weight, with respect to 100 parts by weight of the compound represented by Formula 2, there is a drawback in which polymerization proceeds and a probability of obtaining a polymer having almost no epoxy group is thus high and, when the epichlorohydrin is present in an amount of 1,300 parts by weight or more, excess epichlorohydrin does not participate in reaction, thus having a problem of low production efficiency.

Regarding a weight ratio of the compound represented by Formula 2 and sodium hydroxide in the first step, it is effective that sodium hydroxide is preferably present in an amount of 4 to 13 parts by weight, more preferably 5 to 11 parts by weight, with respect to 100 parts by weight of the compound represented by Formula 2. When the hydroxide salt is present in an amount of less than 4 parts by weight or higher than 13 parts by weight, with respect to 100 parts by weight of the compound represented by Formula 2, there is a drawback of high side reactant content.

A reaction time of the first step is preferably 0.5 to 6 hours, more preferably 2 to 4 hours. When the reaction time is shorter than 0.5 hours, there is a drawback of high polymer content and when the reaction time is longer than 6 hours, there is a drawback of bad color of final products.

The reaction time of the first step is preferably 30 to 100° C., more preferably 60 to 90° C. When the reaction temperature is lower than 60° C., there is a drawback in which polymerization proceeds and molecular weight increases, and when the reaction temperature is higher than 90° C., there is a drawback of increased by-products.

Second Step

This step includes reacting chlorohydrin with epichlorohydrin at a reduced pressure in the presence of a hydroxide salt, which provides reaction conditions enabling cyclization of epichlorohydrin to produce an epoxy group.

In the second step, regarding a weight ratio between the compound represented by Formula 2 and the hydroxide salt, the hydroxide salt is preferably present in an amount of 40 to 70 parts by weight, more preferably 44 to 60 parts by weight, with respect to 100 parts by weight of the compound represented by Formula 2. When the hydroxide salt is present in an amount lower than 40 parts by weight, with respect to 100 parts by weight of the compound represented by Formula 2, there is a drawback in that by-products increase and, when the hydroxide salt is present in an amount higher than 70 parts, a part of the hydroxide salt remains unreacted in the resin, disadvantageously increasing a pH of the resin.

A reaction time of the second step is preferably 2 to 12 hours, more preferably 3 to 6 hours. When the reaction time is shorter than 2 hours, there is a drawback of high polymer content and when the reaction time is longer than 12 hours, there is a drawback of increased by-products.

The reaction time of the second step is preferably 30 to 100° C., more preferably 60 to 90° C. When the reaction temperature is lower than 60° C., there is a drawback in that polymerization proceeds and molecular weight increases, and when the reaction temperature is higher than 90° C., there is a drawback of increased by-products.

The reduced pressure of the second step is preferably 300 to 100 torr, more preferably 180 to 250 torr. When the reduced pressure is lower than 300 torr, excess water remains in the system, thus disadvantageously interrupting reaction and, when the reduced pressure is higher than 100 torr, reflux increases, thus disadvantageously causing increased polymer content.

Third Step

After reaction of the compound represented by Formula 2 with epichlorohydrin, the third step includes stopping stirring and standing for a predetermined time, and then collecting the supernatant using a pump and filtering the same to remove by-products remaining in the resin.

Fourth Step

The fourth step includes collecting epichlorohydrin remaining unreacted with the compound represented by Formula 2. In this case, collection is preferably carried out at 160° C. and 5 to 20 torr.

In another aspect, the present invention provides epoxy resin curing compositions (A, B and C) which include the compound represented by Formula 1 and a curing agent.

The curing agent for the epoxy resin curing composition A may be an acid anhydride curing agent represented by the following Formula 3. The curing agent may include hexahydrophthalic anhydride, phthalic anhydride, methyl tetrahydrophthalic anhydride, anhydrous methyl nadic acid(methyl nadic anhydride), dodecenyl anhydride succinic acid, maleic anhydride, pyromellitic anhydride and anhydrous chlorendic acid and the like.

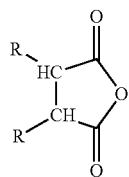

(Formula 3)

wherein R and R' are each independently H or CxHy (in which x and y are a natural number of 1 to 30).

Meanwhile, polycarboxylic acid anhydride having no aromatic nucleus may be, for example, succinic acid anhydride, methyl tetrahydrophthalic anhydride, hexahydrophthalic anhydride, 4-methyl hexahydrophthalic anhydride or the like.

The acid anhydride curing agent that can be used in the present invention may be used alone or in combination of two or more thereof.

In addition, the curing agent for the epoxy resin curing compositions B and C may include a compound having two or more reactive groups reacting with an epoxy group, such as polyamine, polycarboxylic acid anhydride, polyamide and polythiol, or a curing catalyst such as tertiary amine, imidazole, a Lewis acid, an onium salt, dicyandiamide, organic acid dihydrazide or porphine. The compound having two or more reactive groups is preferably polyamine having no aromatic nucleus or polycarboxylic acid anhydride, and the curing catalyst is preferably tertiary amine, imidazole, porphine or an allyl sulfonium salt.

The polyamine is preferably polyamine having two to four amino groups, and the polycarboxylic acid anhydride is preferably dicarboxylic acid anhydride, tricarboxylic acid anhydride and tetra carboxylic acid anhydride.

The polyamine having no aromatic nucleus is preferably an aliphatic polyamine compound or an alicyclic polyamine compound. The polyamine may specifically include ethylenediamine, trimethylene tetramine, tetraethylenepentamine, hexamethylenediamine, polyoxyalkylene polyamine, isophorone diamine, benzenediamine, 3,9-bis(3-aminopropyl)-2,4,8,10-tetraoxaspiro (5.5) undecane or the like. The polyoxyalkylene polyamine is a polyamine having a structure in which a hydroxyl group of polyoxyalkylene polyol is replaced by an amino group and for example includes a compound having two to four amino groups.

The polyamide curing agent used in the present invention may be a compound represented by the following Formula 4.

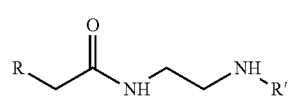

Formula (4)

wherein R and R' are each independently H or CxHy (in which x and y are a natural number of 1 to 30) and n is a natural number of 1 to 100.

In addition, the epoxy resin of the present invention may include a polyether amine curing agent represented by the following Formula 5.

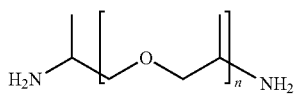

Formula (5)

wherein R and R' are each independently H or CxHy (in which x and y are a natural number of 1 to 30) and n is a natural number of 1 to 100.

The polyether amine may for example include α-(2-aminoethylmethyl) ω-(2-aminomethylethoxy) (JEFFAMINE® D-230, D-400), triethyleneglycoldiamine and an oligomer thereof (JEFFAMINE® XTJ-504, JEFFAMINE® XTJ-512), poly(oxy(methyl-1,2-ethanediyl)), α,α'-(oxydi-2,1-ethanediyl)bis (ω-(isaaminomethylethoxy)) (JEFFAMINE® XTJ-511), bis(3-aminopropyl)polytetrahydrofuran 350, bis(3-aminopropyl)polytetrahydrofuran 750, poly(oxy(methyl-1,2-ethanediyl)), α-hydro-ω-(2-aminomethylethoxy) ether and 2-ethyl-2-(hydroxymethyl)-1,3-propanediol (JEFFAMINE® T-403) and the like.

The epoxy resin curing compositions (A, B and C) of the present invention may include a curing accelerator. The curing accelerator may be any tertiary amine and may more preferably include one or more selected from the group consisting of dimethylaminomethyl phenol, tris(dimethylaminomethyl)phenol, and benzyldimethylamine. In this case, it is possible to maximize curing rate and curing properties.

In addition, the epoxy resin curing compositions (A, B and C) of the present invention may further include an inorganic filler. It is effective that the inorganic filler includes at least one of silica, alumina and talc.

In addition, the epoxy resin curing compositions (A, B and C) of the present invention may further include a variety of additives including a release agent such as a silane coupling agent, stearic acid, palmitic acid, zinc stearate and calcium stearate, and a pigment.

The epoxy resin curing compositions (A, B and C) of the present invention can be produced by thoroughly mixing the mixture in an extruder, a kneader or a roll and then homogenizing the same.

A mix ratio between polyepoxide and the curing agent is preferably an equivalent ratio of the reactive group of the curing agent with respect to epoxy, of about 0.8 to about 1.2. At this ratio, physical properties of the cured substance product may be readily deteriorated.

An epoxy-based resin including a combination of the polyepoxy group and a curing agent may be blended with a reactive additive or a non-reactive additive. The reactive additive may include a compound having one reactive group reacted with epoxy such as alkyl monoamine, a coupling agent having an epoxy group or an amino group, or the like. Regarding the epoxy-based resin including the polyepoxy, the curing agent and the additive, polyepoxide is preferably present in an amount of 4 to 80 wt % with respect to the epoxy-based resin.

The natural material-derived isosorbide epoxy represented by Formula 1 can replace a conventional harmful bisphenol A-based epoxy substance, and uses glycerin-derived epichlorohydrin and is thus derived from 100% natural ingredients, rather than petroleum resources, thus advantageously responding to a high-price oil age and reducing generation of irreversible carbon dioxide and thus advantageously being eco-friendly.

In addition, the present invention has advantages in that natural material-derived epoxy with low viscosity can be produced under optimum process conditions, thereby advantageously realizing equivalent or superior physical properties of cured epoxy to conventional petroleum-derived epoxy substances, despite using natural ingredients as ingredients.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF THE DISCLOSURE

Hereinafter, the present invention will be described with reference to the following Examples, but the present invention is not limited thereto.

Example 1

100 g of isosorbide and 633 g of epichlorohydrin were fed to a 1,000 mL round bottom flask with a cooling tube equipped with a decanter, a stirrer and a nitrogen inlet, and dissolved while heating to 63° C. After the solution in the system was thoroughly dissolved, 11 g of a 50% aqueous sodium hydroxide solution was quantitatively injected for 2 hours to conduct preliminary reaction. Then, 109 g of a 50% aqueous sodium hydroxide solution was quantitatively injected at 65° C. and a reduced pressure of 120 torr over 200 minutes to conduct main reaction.

Water produced during main reaction was continuously removed via the decanter. After completion of main reaction, the reactant was filtered under a reduced pressure with a filter paper and the remaining resin was washed with acetone. The temperature and pressure of the filtered reactant were slowly elevated to 150° C. and 5 torr, and unreacted epichlorohydrin was collected to obtain an epoxy resin of Formula 1 according to the present invention.

Figure 1:
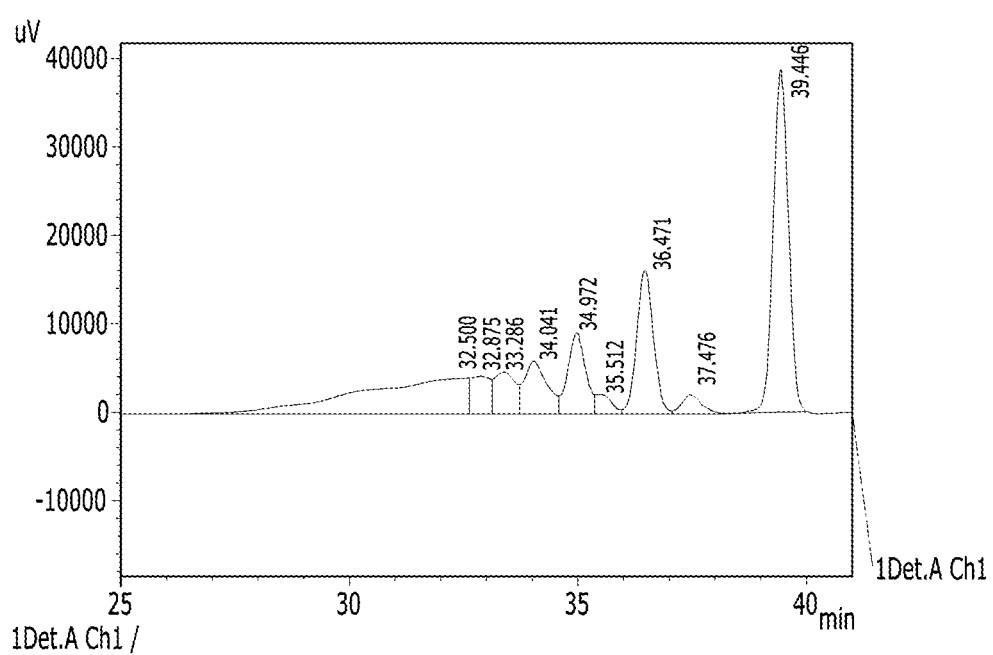
FIGS. 1 to 5 show GPC patterns of epoxy resins produced in Examples 1 to 4, and Comparative Example 1.

In this case, the produced epoxy resin has an epoxy equivalent weight of 184 g/eq, a viscosity of 16,221 cps at 25° C. and a yield of 98% with respect to the theoretical resin value. The molecular weight distribution (GPC) of the epoxy resin is shown in FIG. 1. An area corresponding to a retention time of 39 minutes is epoxy at n=0 and the content thereof is 32%.

Example 2

100 g of isosorbide and 633 g of epichlorohydrin were fed to a 1,000 mL round bottom flask with a cooling tube equipped with a decanter, a stirrer and a nitrogen inlet, and dissolved while heating to 75° C. After the solution in the system was thoroughly dissolved, 11 g of a 50% aqueous sodium hydroxide solution was quantitatively injected for 4 hours to conduct preliminary reaction. Then, 109 g of a 50% aqueous sodium hydroxide solution was quantitatively injected at 75° C. and a reduced pressure of 220 torr over 200 minutes to conduct main reaction.

Water produced during main reaction was continuously removed via the decanter. After completion of main reaction, the reactant was filtered under a reduced pressure with a filter paper and the remaining resin was washed with acetone. The temperature and pressure of the filtered reactant were slowly elevated to 150° C. and 5 torr, and unreacted epichlorohydrin was collected to obtain an epoxy resin of Formula 1 according to the present invention.

Figure 2:
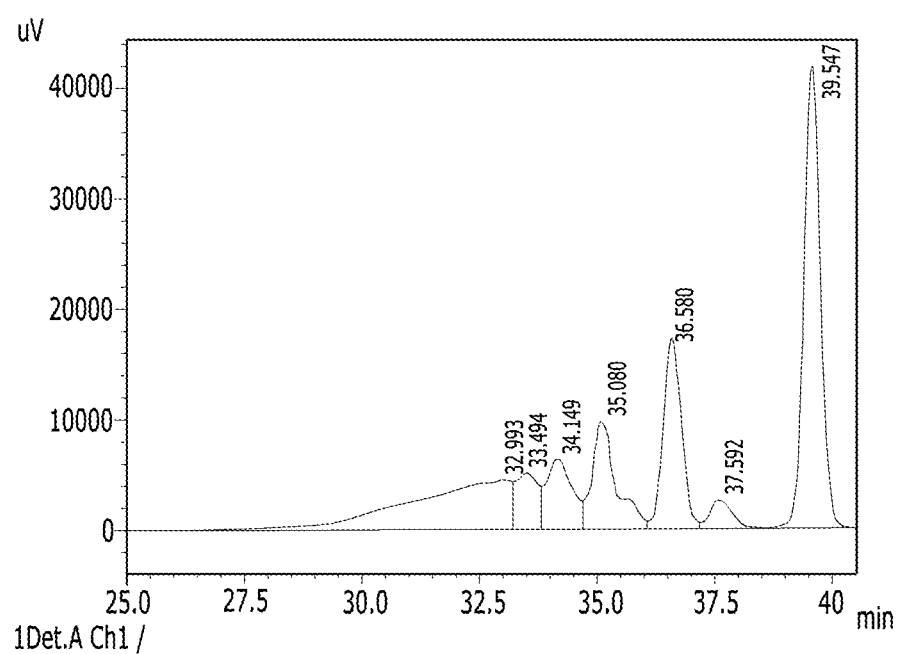

In this case, the produced epoxy resin has an epoxy equivalent weight of 182 g/eq, a viscosity of 8,266 cps at 25° C. and a yield of 98% with respect to the theoretical resin value. The molecular weight distribution (GPC) of the epoxy resin is shown in FIG. 2. An area corresponding to a retention time of 39 minutes is epoxy at n=0 and the content thereof is 34%.

Example 3

100 g of isosorbide and 633 g of epichlorohydrin were fed to a 1,000 mL round bottom flask with a cooling tube equipped with a decanter, a stirrer and a nitrogen inlet, and dissolved while heating to 75° C. After the solution in the system was thoroughly dissolved, 11 g of a 50% aqueous sodium hydroxide solution was quantitatively injected for 2 hours to conduct preliminary reaction. Then, 120 g of a 50% aqueous sodium hydroxide solution was quantitatively injected at 75° C. and a reduced pressure of 220 torr over 7 hours to conduct main reaction.

Water produced during main reaction was continuously removed via the decanter. After completion of main reaction, the reactant was filtered under a reduced pressure with a filter paper and the remaining resin was washed with acetone. The temperature and pressure of the filtered reactant were slowly elevated to 150° C. and 5 torr, and unreacted epichlorohydrin was collected to obtain an epoxy resin of Formula 1 according to the present invention.

Figure 3:
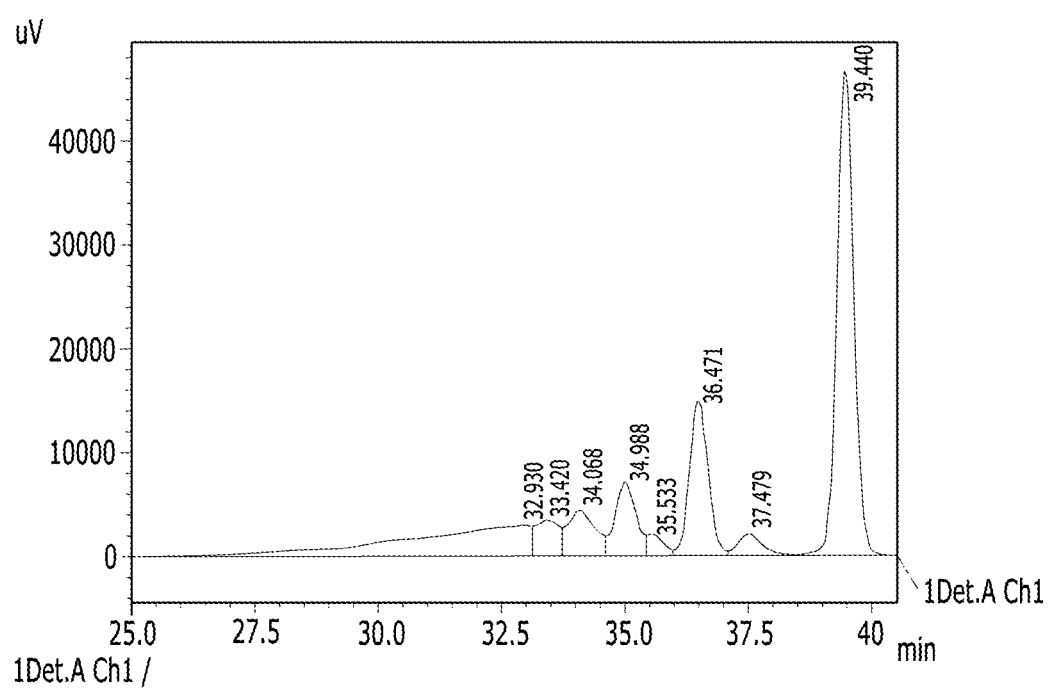

In this case, the produced epoxy resin has an epoxy equivalent weight of 168 g/eq, a viscosity of 4,367 cps at 25° C. and a yield of 98% with respect to the theoretical resin value. The molecular weight distribution (GPC) of the epoxy resin is shown in FIG. 3. An area corresponding to a retention time of 39 minutes is epoxy at n=0 and the content thereof is 42%.

Example 4

100 g of isosorbide and 633 g of epichlorohydrin were fed to a 1,000 mL round bottom flask with a cooling tube equipped with a decanter, a stirrer and a nitrogen inlet, and dissolved while heating to 75° C. After the solution in the system was thoroughly dissolved, 11 g of a 50% aqueous sodium hydroxide solution was quantitatively injected for 2 hours to conduct preliminary reaction. Then, 108 g of a 50% aqueous sodium hydroxide solution was quantitatively injected at 75° C. and a reduced pressure of 220 torr over 200 minutes to conduct main reaction.

Water produced during main reaction was continuously removed via the decanter. After completion of main reaction, the reactant was filtered under a reduced pressure with a filter paper and the remaining resin was washed with acetone. The temperature and pressure of the filtered reactant were slowly elevated to 150° C. and 5 torr, and unreacted epichlorohydrin was collected to obtain an epoxy resin of Formula 1 according to the present invention.

Figure 4:
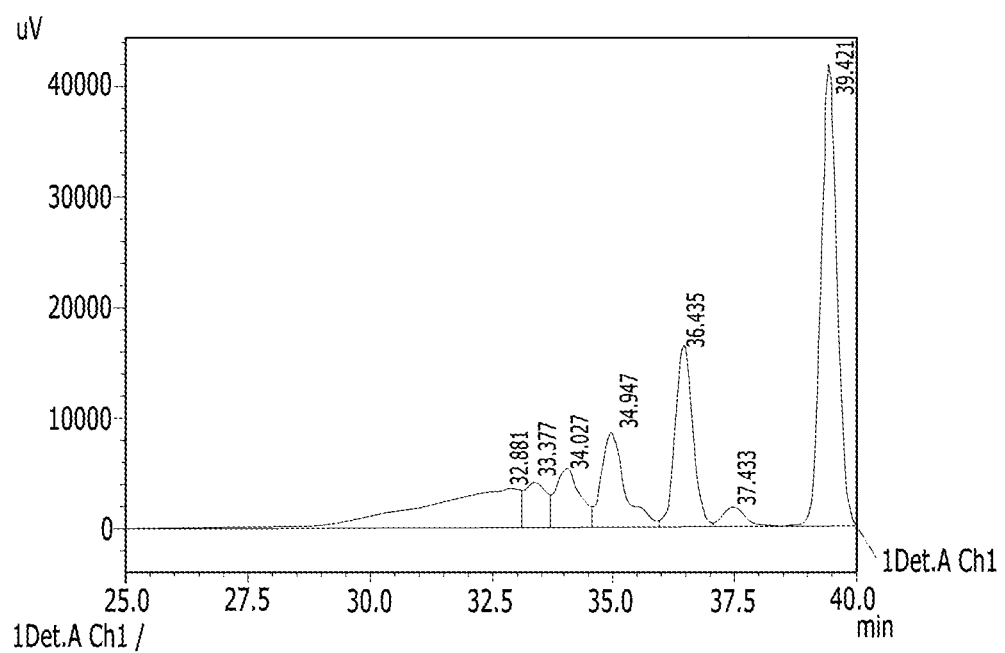

In this case, the produced epoxy resin has an epoxy equivalent weight of 173 g/eq, a viscosity of 3,775 cps at 25° C. and a yield of 98% with respect to the theoretical resin value. The molecular weight distribution (GPC) of the epoxy resin is shown in FIG. 4. An area corresponding to a retention time of 39 minutes is epoxy at n=0 and the content thereof is 39%.

Comparative Example 1

100 g of isosorbide and 1,266 of epichlorohydrin were fed to a 1,000 mL round bottom flask with a cooling tube equipped with a decanter, a stirrer and a nitrogen inlet, and dissolved while heating to 115° C. After the solution in the system was thoroughly dissolved, 120 g of a 50% aqueous sodium hydroxide solution was quantitatively injected for 12 hours to conduct preliminary reaction.

Figure 5:
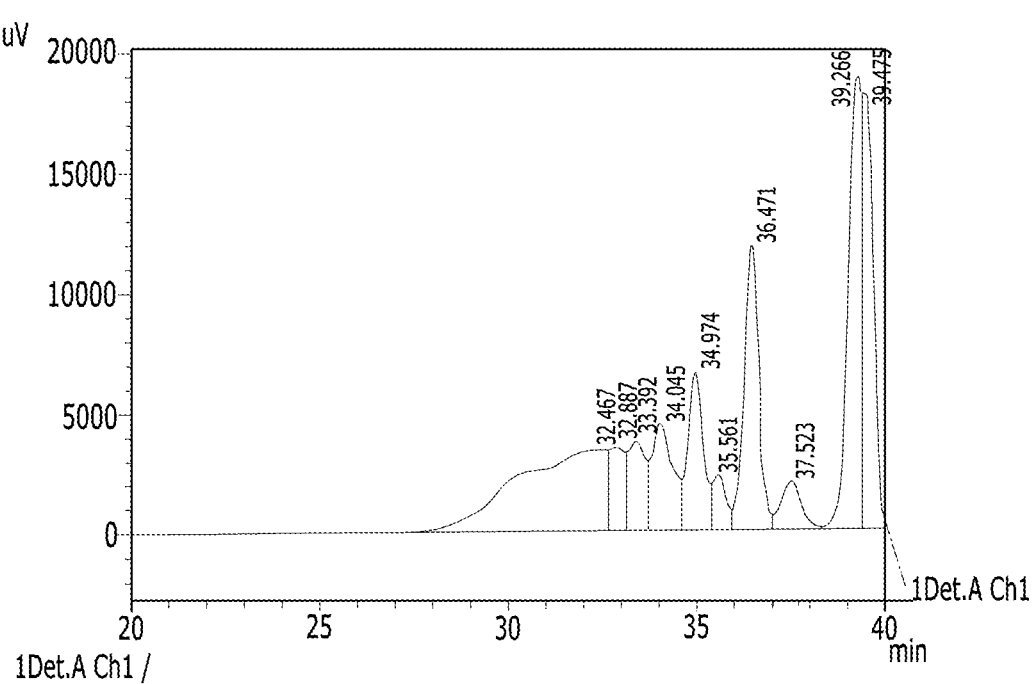

In this case, the produced epoxy resin has an epoxy equivalent weight of 306 g/eq, a viscosity of 13,365 cps at 50° C. and a yield of 98% with respect to the theoretical resin value. The molecular weight distribution (GPC) of the epoxy resin is shown in FIG. 5. An area corresponding to a retention time of 39 minutes is epoxy at n=0 and the content thereof is 34%.

Application Example 1 (Molding for Heavy Electric Equipment)

An isosorbide epoxy resin produced in Example 4 as an epoxy resin, hexahydrophthalic anhydride (hereinafter, referred to as "HHPA"), which is an acid anhydride curing agent, as a curing agent, and benzyldimethylamine (hereinafter, referred to as "BDMA") as a curing accelerator were mixed to prepare an epoxy resin composition (A) of the present invention and the epoxy resin composition (A) was cured at 130° C. for 14 hours.

Comparative Example 2 (Preparation of General Bisphenol A-Type Epoxy Resin Composition and Cured Substance Thereof)

A cured epoxy resin was prepared in the same manner as in Application Example 1, except that YD-128 (available from Kukdo chemical Co., Ltd.) was used as an epoxy resin.

Ingredients of epoxy resin compositions of Application Example 1 and Comparative Example 2, and contents thereof are summarized in Table 1.

TABLE 1

|  | Application Example 1 (content g) | Comparative Example 2 (content g) |
| --- | --- | --- |
| Epoxy resin | Example 4 epoxy (100) | YD-128 (100) |
| Curing agent (HHPA) | 85 | 76 |
| Curing accelerator (BDMA) | 1 | 1 |

The heat resistance, absorbance, tensile strength and tensile modulus, flexural strength and flexural modulus of the cured epoxy resin shown in Table 1 were measured and shown in the following Table 2.

TABLE 2

|  | Application Example 1 | Comparative Example 2 |
| --- | --- | --- |
| Curing agent | HHPA | |
| Curing accelerator | BDMA | |
| Tg (DSC, ° C.) | 108.4 | 134.5 |

TABLE 2-continued

|  | Application Example 1 | Comparative Example 2 |
|---|---|---|
| Flexural strength (MPa) | 114.2 | 134.7 |
| Flexural modulus (MPa) | 2811.9 | 2833.9 |
| Tensile strength (MPa) | 80.3 | 38.1 |
| Tensile modulus (MPa) | 3146.3 | 3866.3 |
| Elongation (%) | 5.3 | 1.5 |
| Absorbance (%) | 0.55 | 0.21 |

Measurement of heat resistance: Tg (glass transition temperature) was measured by DSC analysis.

Measurement of absorbance: Variation in weight after storing in 25° C. distilled water for 72 hours was measured.

Measurement of tensile strength and tensile modulus: specimen was prepared in accordance with ASEM 638, the width and thickness of the specimen were measured with a micrometer and tensile strength and tensile modulus were measured using a U.T.M tester.

Measurement of flexural strength and flexural modulus: a specimen was prepared, the width and thickness of the specimen were measured with a micrometer, and flexural strength and flexural modulus were measured using a U.T.M tester.

As can be seen from Table 2, when the epoxy resin according to the present invention is used, moldings that exhibit similar flexural strength, but 3 times or higher elongation, as compared to petroleum-derived bisphenol A-type epoxy can be produced.

Application Example 2 (Adhesives Debonded in Water)

The isosorbide epoxy resin produced in Example 4 as an epoxy resin was mixed with G-5022X70 (available from Kukdo chemical Co., Ltd.), which is a polyamide curing agent, as a curing agent, to form a thin film with a thickness of 150 μm on an iron substrate, thereby producing an epoxy resin composition (B) of the present invention. The epoxy resin composition (B) was cured at room temperature for 24 hours and at 80° C. for 2 hours.

Comparative Example 3 (Preparation of General Bisphenol A-Type Epoxy Resin Composition and Cured Substance Thereof)

A cured epoxy resin was prepared in the same manner as in Application Example 2, except that YD-128 (available from Kukdo chemical Co., Ltd.) was used as an epoxy resin.

Ingredients of epoxy resin compositions of Application Example 2 and Comparative Example 3, and contents thereof are summarized in Table 3.

TABLE 3

|  | Application Example 2 (content g) | Comparative Example 3 (content g) |
|---|---|---|
| Epoxy resin | Example 4 epoxy (100) | YD-128 (100) |
| Curing agent (G-5022X70) | 144.5 | 134.4 |

The heat resistance, absorbance, adhesive strength and water debonding test of cured epoxy resins shown in Table 3 were measured and shown in the following Table 4.

TABLE 4

|  | Application Example 2 | Comparative Example 3 |
|---|---|---|
| Curing agent | G-5022X70 | |
| Tg (DSC, ° C.) | 64.5 | 66.7 |
| Absorbance (%) | 33 | 1 |
| Adhesion (cross cut) | 100/100 | 100/100 |
| Water debonding test (70° C.) | 30 sec or less | 7 days or longer |

Measurement of heat resistance: Tg (glass transition temperature) was measured by DSC analysis.

Measurement of absorbance: Variation in weight after storing in 25° C. distilled water for 72 hours was measured.

Measurement of adhesive strength: a line was drawn with a cutter on a coated substrate to prepare a 100-square grid, and immediately after a sharp tape was attached to the line, the tape was peeled off and then the number of squares remaining on the substrate was recorded (ASTM D3359)

Water debonding test: after x-cut was made on a coated substrate and immersed in 70° C. water, a time by during which a coating film was peeled off was measured.

As can be seen from Table 4, in a case in which the epoxy resin according to the present invention was used, as compared to petroleum-derived and based bisphenol A-type epoxy, the epoxy resin exhibited similar adhesive strength, but exhibited rapid deterioration in adhesive strength when immersed in hot water. Accordingly, based on this property, the epoxy resin was applicable as an adhesive agent for debonding an article due to rapidly deteriorated adhesive strength in wet environments while requiring excellent adhesive strength in dry environments.

Application Example 3 (Anti-Fog Absorbance Coating)

The isosorbide epoxy resin produced in Example 4 as an epoxy resin was mixed with polyoxyalkylene triamine (JEFFAMINE T-403, available from Huntsman Specialty Chemicals Corp.) as a curing agent, to form a thin film with a thickness of 150 μm on a glass substrate, thereby producing an epoxy resin composition (C) of the present invention.

The epoxy resin composition (C) was cured at room temperature for 24 hours and at 80° C. for 2 hours.

Comparative Example 4 (Preparation of General Aliphatic Polyglycidyl Ether Composition and Cured Substance Thereof)

A cured epoxy resin was prepared in the same manner as in Comparative Example 3, except that 57 g of an aliphatic polyglycidyl ether compound (DE-211, available from Hajin chemtech Co., Ltd.) was used as an epoxy resin.

Absorbance and fog resistance test was conducted by standing a specimen at 20° C. and at a relative humidity of 50% for one hour and then placing the specimen above 40° C. warm water and measuring a time by which penetration distortion by a water film was considered to occur. Commonly, a soda lime glass with no anti-fogging treatment was fogged within 2 to 5 seconds. An anti-fog property of 50 seconds or longer was practically required to prevent fogging. Preferably, an anti-fog property was 70 seconds or longer, more preferably 100 seconds or longer.

Ingredients of epoxy resin compositions of Application Example 3 and Comparative Example 4, and contents and anti-fog property thereof are summarized in Table 5.

TABLE 5

|  | Application Example 3 (content g) | Comparative Example 4 (content g) |
|---|---|---|
| Epoxy resin | Example 4 epoxy (100) | DE-211 (100) |
| Curing agent | 42.3 | 57 |
| Absorbance anti-fog property (second) | (JEFFAMINE T-403) 600 sec or more | (G-5022X70) 180 sec |

As can be seen from Table 5, the epoxy resin according to the present invention exhibited 3 times or more superior properties in absorbance anti-fog property test, as compared to conventional aliphatic polyglycidyl ether compounds, thus being applicable to anti-fog films.

The natural material-derived isosorbide epoxy represented by Formula 1 according to the present invention can replace a bisphenol A-based epoxy substance, and uses glycerin-derived epichlorohydrin and is thus derived from 100% natural ingredients, rather than petroleum resources, thus advantageously responding to a high-price oil age and reducing generation of irreversible carbon dioxide and thus advantageously being eco-friendly.

In addition, the present invention has advantages in that natural material-derived epoxy with low viscosity can be produced under optimum process conditions, thereby advantageously realizing equivalent or superior physical properties of cured epoxy to conventional petroleum resource-derived epoxies, despite using natural ingredients as ingredients.

What is claimed is:

1. A method of preparing natural material-derived epoxy resin represented by the following Formula 1, the method comprising:
    a first step including mixing 550 to 650 parts by weight of epichlorohydrin (ECH) obtained from glycerin as a starting material with 100 parts by weight of a compound represented by the following Formula 2, dissolving the mixture at an elevated temperature of 60 to 75° C., adding 5 to 11 parts by weight of sodium hydroxide (NaOH) to 100 parts by weight of a compound represented by the following Formula 2 and conducting preliminary reaction for 2 to 4 hours;
    a second step including conducting main reaction of the reactants of the first step at a temperature of 60 to 75° C. and at a reduced pressure of 180 to 250 torr, the main reaction being carried out for 3 to 6 hours by adding 44 to 60 parts by weight of sodium hydroxide (NaOH) to 100 parts by weight of the compound represented by the following Formula 2;
    a third step including standing the reaction solution after reaction of the second step, separating the supernatant by reverse aliquoting and filtering the same; and
    a fourth step including collecting epichlorohydrin from the filtrate

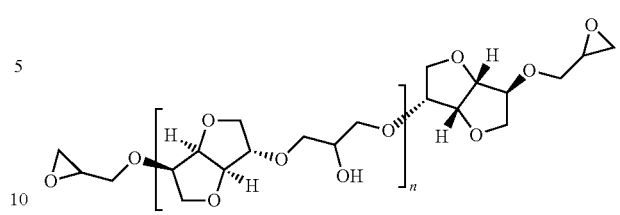

(Formula 1)

wherein n is a natural number of 0 to 300,

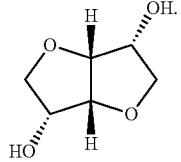

(Formula 2)

2. A method of preparing a coating composition of a natural material-derived epoxy resin to have anti-fog property, the method comprising:
    obtaining epichlorohydrin (ECH) from glycerin as a starting material;
    conducting a reaction of the epichlorohydrin (ECH) with a compound represented by the following Formula 2 to obtain a natural material-derived epoxy resin represented by the following Formula 1; and
    curing the natural material-derived epoxy resin by mixing polyoxyalkylene triamine with the natural material-derived epoxy resin,
    wherein the reaction includes:
    a first reaction conducted at a temperature of 60 to 90° C. for 2 to 4 hours in the presence of sodium hydroxide (NaOH); and
    a second reaction conducted, for 3 to 6 hours, at a temperature of 6 to 90° C. and at a pressure of 180 to 250 torr

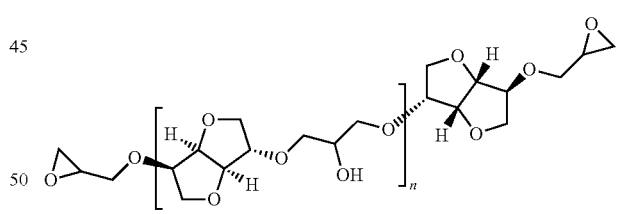

(Formula 1)

wherein n is a natural number of 0 to 300,

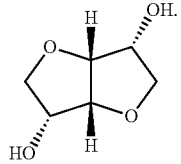

(Formula 2)

* * * * *